United States Patent [19]
Sonigo et al.

[11] Patent Number: 6,020,123
[45] Date of Patent: Feb. 1, 2000

[54] OLIGONUCLEOTIDE SEQUENCES FOR THE AMPLIFICATION OF THE GENOME OF THE RETROVIRUSES OF THE HIV-2 AND SIV TYPE, AND THEIR USES FOR IN VITRO DIAGNOSIS OF THE INFECTIONS DUE TO THESE VIRUSES

[75] Inventors: Pierre Sonigo; Christian Brechot; Valérie Courgnaud, all of Paris, France

[73] Assignees: Institut Pasteur; Institut National de la Sante et de la Recherche Medicale, both of Paris, France

[21] Appl. No.: 08/343,998

[22] Filed: Nov. 18, 1994

Related U.S. Application Data

[63] Continuation of application No. 07/820,600, filed as application No. PCT/FR90/00394, Jun. 5, 1990, abandoned.

[30] Foreign Application Priority Data

Jun. 2, 1989 [FR] France .................................. 8907355

[51] Int. Cl.$^7$ ............................ C12Q 1/68; C07H 21/00; C12N 15/09; C12P 19/34
[52] U.S. Cl. ........................... 435/6; 435/69.1; 435/91.2; 536/24.33
[58] Field of Search .................................. 435/5, 6, 69.1, 435/91.2, 172.3; 536/24.33; 935/77, 78

[56] References Cited

U.S. PATENT DOCUMENTS

| | | | |
|---|---|---|---|
| 4,683,195 | 7/1987 | Mullis et al. | 435/6 |
| 4,839,288 | 6/1989 | Montagnier et al. | 435/235.1 |
| 5,051,496 | 9/1991 | Allizon et al. | 430/324 |

FOREIGN PATENT DOCUMENTS

| | | |
|---|---|---|
| 229701 | 1/1987 | European Pat. Off. . |
| 269445 | 6/1988 | European Pat. Off. . |
| WO 86/02383 | 4/1986 | WIPO . |
| 87/07300 | 12/1987 | WIPO . |
| 87/07906 | 12/1987 | WIPO . |
| 88/01302 | 2/1988 | WIPO . |

OTHER PUBLICATIONS

Linz et al. "Systematic Studies on Parameters Influencing the Performance of the Polymerase Chain Reaction" J. Clin. Chem. Clin. Biochem. 28(1):5–13, Jan. 1990.

Rayfield et al. "Mixed Human Immunodeficiency Virus (HIV) Infection in an Individual" J Infec. Dis. 158(6):1170–1176, Dec. 1988.

Chakrabarti et al. "Sequence of Simian Immunodeficiency Virus . . . " Nature 328:543–547, Aug. 1987.

Maniatis et al. "Molecular Cloning—A Laboratory Manual" Cold Spring Harbor Laboratory, pp. 412–421, 1982.

Courgnaud et al. "Genetic Differences Accounting for Evolution and Pathogenicity of Simian Immunodeficiency Virus" J. Virol. 66(1): 414–419, Jan. 1992.

Horsburgh, Jr., et al., "Duration of Human Immunodeficiency Virus Infection Before Detection of Antibody," The Lancet, 2, 637–639 (1989).

Ou et al., "DNA Amplification for Direct Detection of HIV–1 in DNA of Peripheral Blood Mononuclear Cells," Science, 239, 295–297 (1988).

Rayfield et al., "Mixed Human Immunodeficiency Virus (HIV) Infection in an Individual: Demonstration of both HIV Type 1 and Type 2 Proviral Sequences by Using Polymerase Chain Reaction," The Journal of Infectious Diseases, 158, 6, 1170–1176 (1988).

Kemp et al., "Colorimetric Detection of Specified DNA Segments Amplified by Polymerase Chain Reactions," Proc. Natl. Acad. Sci. USA, 86, 2423–2427 (1989).

Meyerhans et al., "Temporal Fluctuations in HIV Quasispecies In Vivo are Not Reflected by Sequencial HIV Isolations," Cell, 58, 901–910 (1989).

Maniatis et al., Molecular Cloning—A Laboratory Manual, Cold Spring Harbor Laboratory, 1982, p. 412–421.

Chakrabarti et al., "Sequence of simian immunodeficiency virus from macaque and its relationship to other human and simian retroviruses", Nature, vol. 328, pp. 543–547 (1987).

Guyader et al., "Genome organization and transactivation of the human immunodeficiency virus type 2", Nature, vol. 326, pp. 662–670 (1987).

*Primary Examiner*—George C. Elliott
*Assistant Examiner*—Thomas G. Larson
*Attorney, Agent, or Firm*—Finnegan, Henderson, Farabow, Garrett & Dunner, L.L.P.

[57] ABSTRACT

The invention relates to oligonucleotide sequences (or initiators) derived from the HIV-2 ROD virus genome and from that of the SIV-mac 142 virus, as well as their use in an in vitro method for the diagnosis of the infection of an individual by a HIV-2 type virus.

18 Claims, No Drawings

OLIGONUCLEOTIDE SEQUENCES FOR THE AMPLIFICATION OF THE GENOME OF THE RETROVIRUSES OF THE HIV-2 AND SIV TYPE, AND THEIR USES FOR IN VITRO DIAGNOSIS OF THE INFECTIONS DUE TO THESE VIRUSES

This application is a continuation, of application Ser. No. 07/820,600, filed Jan. 22, 1992, now abandoned, which is a national stage application of PCT/FR90/00394, filed Jun. 5, 1990.

The present invention relates to oligonucleotide sequences which can be used in particular as oligonucleotide primers for the implementation of procedures for the amplification of nucleotide sequences of human immunodeficiency retroviruses of the HIV-2 type, or monkey immunodeficiency retroviruses of the SIV type.

The invention relates in particular to the use of these sequences in methods for in vitro diagnosis in man of the infection of an individual by a retrovirus of the HIV-2 type.

The isolation and characterization of retroviruses grouped together under the designation HIV-2 were described in the European patent application No. 87/400.151.4. These retroviruses had been isolated from several African patients exhibiting symptoms of a lymphadenopathy or an Acquired Immunodeficiency Syndrome (AIDS).

The retroviruses of the HIV-2 type like the retroviruses of the HIV-1 type are characterized by a tropism for the human T4 lymphocytes and by a cytopathogenic effect with regard to these lymphocytes when they multiply within them to give rise to either generalized and persistent polyadenopathies, or an AIDS.

Another retrovirus, designated SIV-1, this designation replacing designation STLV-III, used earlier, was isolated from the rhesus macaque monkey (M. D. DANIEL et al. Science, 228, 1201 (1985); N. L. LETWIN et al., Science, 230, 71 (1985) referred to as "STLV-IIImac").

Another retrovirus, designated "STLV-$III_{AGM}$" (or $SIV_{AGM}$), was isolated from wild green monkeys. However, unlike the viruses present in the rhesus macaque monkey, the presence of STLV-$III_{AGM}$ does not seem to induce a disease of the AIDS type in the African green monkey.

For reasons of semantics, these viruses will be designated in the remainder of the description only by the expression SIV (the expression SIV is an English abbreviation for "Simian Immunodeficiency Virus", possibly followed by an abbreviation indicating the species of monkey from which they are derived, for example "MAC" for the "macaque" or "AGM" for the "African Green Monkey".

A strain of the retrovirus SIV-1mac was deposited with the C.N.C.M. on Feb. 7, 1986 under No. I-521.

Studies have shown that the SIV-1 retrovirus contains certain proteins possessing immunological relatedness to proteins or glycoproteins which can be obtained under similar conditions from HIV-2.

The continuation of the study of the HIV-2 retroviruses has also led to the production of DNA sequences complementary (cDNAs) to the RNAs of their genome. The complete nucleotide sequence of a cDNA of a representative retrovirus of the class HIV-2 (HIV-2 ROD) was deposited on Feb. 21, 1986 with the C.N.C.M. under No. I-532, under the reference name of LAV-2 ROD.

The methods of in vitro diagnosis of the infections by viruses of the HIV-2 type presently practised, are most often based on the detection of anti-HIV-2 antibodies possibly present in a biological fluid, in particular in a serum obtained from the patient under study, by placing this biological fluid in contact with extracts or antigens of HIV-2 under conditions leading to the production of a possible immunological reaction of these extracts or antigens with these antibodies.

Such diagnostic methods are relatively insensitive and risk giving false negatives, in particular in the case of a recent infection of an individual by the HIV-2 virus.

The techniques of genomic amplification make a considerable contribution to the development of particularly sensitive methods of in vitro diagnosis of viral diseases. Among such amplification techniques, mention may be made of the PCR (Polymerase Chain Reaction) technique as described in the European patent applications No. 86/302.298.4 of Mar. 27, 1986 and No. 87/300.203.4 of Jan. 09, 1987, and also the technique known as "Qβreplicase" described in Biotechnology, vol. 6 page 1197 (October 1988), and entailing the use of a RNA polymerase (T7RNA polymerase) described in the International patent application No. WO89/01050. They make it possible to improve the sensitivity of detection of the nucleic acids of the virus, but do, however, require the use of specific primers for synthesis.

In the case of the research on viruses of the HIV type, the choice of primers poses problems. In fact, on account of the great variability in the nucleotide sequences of the viral genome, a primer corresponding to a known sequence of a given isolate of HIV-2 may fail in the amplification of certain viral variants of the HIV type. Furthermore, even if a primer is selected from a region of the genome conserved from one HIV-2 virus to another, its "efficiency" is not thereby assured and may give rise to poor amplification yields.

It is precisely the aim of the present invention to provide oli,gonucleotide sequences (or primers) which make possible the amplification of the genome of any virus of the HIV-2 type in good yields for diagnostic purposes.

The primers of the present invention are specific both for the viruses of the HIV-2 group and the viruses of the SIV type, and are insensitive to variations in the genome of these viruses.

The object of the present invention is oligonucleotide primers of about 15 to 30 nucleotides which can be used for the genomic amplification of the viruses of the HIV-2 or SIV type.

A primer according to the invention is characterized in that its nucleotide sequence is:

either selected from those which are contained in one of the nucleotide sequences delimited by the nucleotides situated at the positions 40 and 61 (GGTTCTCTCCAGCACTAGCAGG; SEQ ID NO:1), 9537 and 9558 (GGTTCTCTCCAGCAGTAGCAGG; SEQ ID NO:17), 240 and 259 (GACCCTGGTCTGTTAGGACC; SEQ ID NO:18), 546 and 569 (ATGGGCGCGAGAAACTCCGTCTTG; SEQ ID NO:3), 906 and 927 (ACAAGTAGACCAACAGCACCAT; SEQ ID NO:19), 612 and 633 (CCCGGCGGAAAGAAAAAGTACA; SEQ ID NO:5), 1857 and 1876 (TGGGGAAAGAAGCCCCGCAA; SEQ ID NO:7), 2078 and 2101 (GCTGCACCTCAATTCTCTCTTTGG; SEQ ID NO:20), 6275 and 6299 (CAGAAATAGGGATACTTGGGGAACC; SEQ ID NO:9), 6855 and 6878 (TGTAATGATACCAATTATTCAGGC; SEQ ID NO:11), 7548 and 7573

(ACCTTTAGTGCAGAGGTGGCAGAACT; SEQ ID NO:21), 7782 and 7805 (GGGATAGTGCAGCAACAGCAACAG; SEQ ID NO:13), 8412 and 8434 (CATTTCCTGATCCGCCAGCTGAT; SEQ ID NO:14), 61 and 82 (GTAGAGCCTGGGTGTTCCCTGC; SEQ ID NO:22), 9558 and 9579 (GTAGAGCCTGGGTGTTCCCTGC; SEQ ID NO:22) of the cDNA derived from the genome of the HIV-2 ROD virus, or which are complementary to one of the above-mentioned nucleotide sequences, or selected from those which are contained in one of the nucleotide sequences delimited by the nucleotides situated at the positions 40 and 61 (GGTTCTCTCCAGCACTAGCAGG; SEQ ID NO:1), 9511 and 9532 (GGTTCTCTCCAGCACTAGCAGG; SEQ ID NO:1), 240 and 259 (GACCCTGGTCTGTTAGGACC; SEQ ID NO:18), 256 and 275 (GACCCTGGTCTGTTAGGACC; SEQ ID NO:18), 551 and 574 (ATGGGCGCGAGAAACTCCGTCTTG; SEQ ID NO:3), 911 and 932 (ACAAGTAGACCAACAGCACCAT; SEQ ID NO:19), 617 and 638 (CCCGGCGGAAAGAAAAAGTACA; SEQ ID NO:5), 1868 and 1887 (TGGGGAAAGAAGCCCCGCAA; SEQ ID NO:7), 2035 and 2058 (GCTGCACCTCAATTCTCTCTTTGG; SEQ ID NO:20), 6227 and 6251 (CAAGAATAGGGATACTTGGGGAACA; SEQ ID NO:23), 7550 and 7564 (AGAGGTGGCAGAACT; SEQ ID NO:24), 7776 and 7799 (GGGATAGTGCAGCAACAGCAACAG; SEQ ID NO:13), 8406 and 8428 (CATTTCCTGATCCGCCAACTGAT; SEQ ID NO:25), 61 and 82 (GTAGAGCCTGGGTGTTCCCTGC; SEQ ID NO:22); 9532 and 9553 (GTAGAGCCTGGGTGTTCCCTGC; SEQ ID NO:22) of the cDNA derived from the genome of the SIVmac 142 virus, or which are complementary to one of the above-mentioned nucleotide sequences, or (in particular in the case of the longest primers) contains one of the above-mentioned nucleotide sequences derived from HIV-2 ROD or SIVmac 142, or contains a nucleotide sequence complementary to one of these latter sequences, it being understood that the possible additional nucleotides which "extend beyond" the nucleotide sequence of the type in question preferably at the 5' end, preferably coincide with those which are placed external to the 5' end of the same sequence within the complete sequence of HIV-2 ROD or SIVmac 142, it also being understood that the strands of the cDNAs which are taken into consideration are those which are found to be complementary to the RNAs of the HIV-2 ROD and SIVmac 142 viruses, or, if the sequence of this primer is not identical with one of the the above-mentioned nucleotide sequences, or is not complementary with one of these sequences, nonetheless capable of hybridizing with this nucleotide sequence derived from the HIV-2ROD and/or SIVmac 142 viruses mentioned above in a solution composed of 10 mM Tris, 20 my KCl, 2 nM MgCl$_2$, and 0.01% gelatin for 1 minute at a temperature equal to or higher than 50° C.

The numbering of the nucleotides mentioned above corresponds to that used in FIG. 2 of the article by GUYADER et al., Nature, vol. 326, p. 662–669 (1987) in the case if the cDNA of HIV-2 ROD and to that used in FIG. 1 of the article by CHAKRABARTI L. et al., Nature, vol. 328, p. 543–547 (1987) in the case of the cDNA of SIVmac 142.

The invention relates more particularly to the oligonucleotide primers characterized by the following nucleotide sequences (shown in the 5'→3' sense;

| LTR1 | GGTTCTCTCCAGCACTAGCAGG, | SEQ ID NO: 1, |
|---|---|---|
| LTR2 | GGTCCTAACAGACCAGGGTC, | SEQ ID NO: 2, |
| GAG1 | ATGGGCGCGAGAAACTCCGTCTTG, | SEQ ID NO: 3, |
| GAG5 | ATGGTGCTGTTGGTCTACTTGT, | SEQ ID NO: 4, |
| GAG2 | CCCGGCGGAAAGAAAAAGTACA, | SEQ ID NO: 5, |
| GAG2B | TGTACTTTTTCTTTCCGCCGGG, | SEQ ID NO: 6, |
| POL1 | TGGGGAAAGAAGCCCCGCAA, | SEQ ID NO: 7, |
| POL2 | CCAAAGAGAGAATTGAGGTGCAGC, | SEQ ID NO: 8, |
| P1 | CAGAAATAGGGATACTTGGGGAACC, | SEQ ID NO: 9, |
| P2 | GCCTGAATAATTGGTATCATTACA, | SEQ ID NO: 10, |
| P2B | TGTAATGATACCAATTATTCAGGC, | SEQ ID NO: 11, |
| P4 | AGTTCTGCCACCTGTGCACTAAAGG, | SEQ ID NO: 12, |
| P6 | GGGATAGTGCAGCAACAGCAACAG, | SEQ ID NO: 13, |
| P7 | CATTTCCTGATCCGCCAGCTGAT, | SEQ ID NO: 14, |
| P7B | ATCAGCTGGCGGATCAGGAAATG, | SEQ ID NO: 15, |
| P8 | GCAGGGAACACCCAGGCTCTAC, | SEQ ID NO: 16, |

The above-mentioned primers are identical with or complementary to the following nucleic acid sequences, derived from the cDNA of the HIV-2 ROD virus or from that of the SIVmac 142 virus:

the primer LTR1 is identical, on the one hand, with the nucleotide sequence comprising the nucleotides situated at the positions 40–61, as well as with that comprising the nucleotides situated at the positions 9537 to 9558 of the cDNA of HIV-2 ROD and, on the other, to the nucleotide sequence comprising the nucleotides situated at the positions 40 to 61 as well as that comprising the nucleotides situated at the positions 9511 to 9532 of the cDNA of SIVmac 142, the primer LTR2 is complementary, on the one hand, to the nucleotide sequences comprising the nucleotides situated at the positions 240 to 259 of the cDNAs of HIV-2 ROD and SIVmac 142 and, on the other, to the nucleotide sequence comprising the nucleotides situated at the positions 256 to 275 of the cDNA of SIVmac 142, the primer GAG1 is identical with the nucleotide sequence comprising the nucleotides 546 to 569 of the cDNA of HIV-2 ROD and with the nucleotide sequence comprising the nucleotides situated at the positions 551 to 574 of the cDNA of SIVmac 142, the primer GAG5 is complementary to the nucleotide sequences comprising the nucleotides situated at the positions 906 to 927 and 911 to 932 of the cDNAs of HIV-2 ROD and SIVmac 142, respectively, the primer GAG2 is identical with the nucleotide sequences comprising the nucleotides situated at the positions 612 to 633 and 617 to 638 of the cDNAs of HIV-2 ROD and SIVmac 142, respectively, the primer GAG2B is complementary to the nucleotide sequences mentioned above to be identical with GAG2, the primer POL1 is identical with the nucleotide sequences comprising the nucleotides situated at the positions 1857 to 1876 and 1868 to 1887 of the cDNAs of HIV-2 ROD and SIVmac 142, respectively, the primer P1 is identical with the nucleotide sequences comprising the nucleotides situated at the positions 6275 to 6299 and 6227 to 6251 of the cDNAs of HIV-2 ROD and SIVmac 142, respectively, the primer P2 is complementary to the nucleotide sequence comprising the nucleotides situated at the positions 6855 to 6878 of the cDNA of HIV-2 ROD, the primer P2B is complementary to the nucleotide sequence which is identical with P2 mentioned above, the primer P4 is complementary to the nucleotide sequence comprising the nucleotides situated at the positions 7548 to 7573 of the cDNA of HIV-2 ROD, and partially, complementary to the nucleotide sequence comprising the nucleotides situated at the positions 7550 to 7564 of the cDNA of SIVmac 142, the primer P6 is identical with the nucleotide sequences comprising the nucleotides situated at the positions 7782 to 7805 and 7776 to 7799 of the cDNAs of HIV-2 ROD and SIVmac 142, respectively, the primer P7 is identical with the nucleotide sequences comprising the nucleotides situated at the positions 8412 to 8434 and 8406 to 8428 of the cDNAs of HIV-2 ROD and SIVmac 142, respectively, the P7B primer is complementary to the nucleotide sequences which are identical with the primer P7 mentioned above, the primer P8 is complementary, on the one hand, to the nucleotide sequence comprising the nucleotides situated at the positions 61 to 82 as well as to that comprising those situated at the positions 9558 to 9579 of the cDNA of HIV-2 ROD and, on the other, to the nucleotide sequence comprising the nucleotides situated at the positions 61 to 82 as well as to that comprising nucleotides situated at the positions 9532 to 9553 of the cDNA of the SIVmac 142.

The object of the invention is also the primers possessing a complementary nucleotide structure to those of the primers LTR1, LTR2, GAG1, GAG5, POL1, POL2, P1, P4 and P8 defined above.

The invention also relates to the primers exhibiting certain mutations in comparison with those defined above without the hybridization properties, such as defined above, of these primers being modified. The percentage of nucleotides different from those constituting the primers described above without thereby effecting the hybridization properties of the primers of the invention usually lies between 0% and 10%, and preferably does not exceed 20%.

Generally speaking, a larger number of mutations is tolerated at the 5' end than at the 3' end of the primer, since the 3' end must hybridize perfectly with a specific strand of a nucleotide sequence in order to make possible the amplification of this sequence.

The invention also extends to the primers such as those described above linked at their 5' end to a promoter for the implementation of a method of genomic amplification by the synthesis of multiple copies of RNA such as described in the European patent application No. 88/307.102.9 of Jan. 8, 1988.

The object of the invention is more particularly the use of the primers described above for the implementation of a method of in vitro diagnosis of the infection of an individual by a virus of the HIV-2 type.

This method of in vitro diagnosis of the invention is carried out starting from a biological sample (in particular a biological fluid such as serum) obtained from a patient under study, and comprises mainly the following steps:

a step involving the extraction of the nucleic acid to be detected belonging to the genome of the virus of the HIV-2 type possibly present in the above-mentioned biological sample and, where appropriate, a step in which the said nucleic acid is treated with a reverse transcriptase if the nucleic acid is in the form of RNA in order to produce a double-stranded nucleic acid, a cycle comprising the following steps:
  denaturation of the double-stranded nucleic acid to be detected, which leads to the formation of single-stranded nucleic acids,
  hybridization of each of the single-stranded nucleic acids obtained during the preceding denaturation step with at least one primer according to the invention, by placing the above-mentioned strands in contact with at least one primer couple according to the invention under the conditions of hybridization defined above,
  formation, from the primers, of the DNAs complementary to the strands to which they are hybridized (elongation step) in the presence of a polymerization agent and the four different nucleoside triphosphates, which leads to the formation of a larger number of double-stranded nucleic acids to be detected than were present at the preceding denaturation step, this cycle being repeated a defined number of times in order to produce the said nucleic acid to be detected possibly present in the biological sample in an amount sufficient to permit its detection, a step involving the detection of the possible presence of the nucleic acid belonging to the genome of a virus of the HIV-2 type in the biological sample.

The method of in vitro diagnosis of the invention may be performed starting either from the RNA or from the viral DNA.

In fact, the genomes of the HIV-2 viruses exist in the form of RNA or DNA, depending on the localization of the virus in the organism.

When the virus is situated within the cells of the organism, in particular in the interior of blood cells, its RNA is recopied into DNA by a reverse transcriptase. On the other hand, the genome of the viruses of the HIV-2 type in an extracellular environment, in particular in the blood, remains in the RNA form.

The step involving the extraction of the viral DNA contained in the cells of the biological sample is given in detail more particularly in the article by LAURE F. et al., published in Lancet, p. 538–540 (1988).

As an illustration, the lymphocytes are separated from other blood constituents by centrifugation in a Ficoll gradient. The lymphocytes thus obtained are then treated with a lysis buffer consisting of 10 mM Tris pH 8, 10 mM EDTA, 10 mM NACl, 0.5% SDS (sodium dodecylsulfate) and 100 $\mu$g/ml of proteinase K for 2 hours at 60° C. The DNA is then extracted with phenol and precipitated with ethanol.

The extraction may also be carried out on concentrated serum in a manner identical with that previously described. In this case the RNA is obtained and it is necessary to carry out an additional step to transform the single-stranded RNA into double-stranded DNA when the in vitro diagnosis of the invention is performed on biological samples containing the viruses of the HIV-2 type, the genomes of which are in the RNA form.

This transformation of the RNA into DNA is performed by treatment of the RNA obtained after extraction of the biological sample, in particular serum, in a suitable medium with the aid of an enzyme, reverse transcriptase, under the conditions given by the supplier (Amersham, for example).

In a preferred embodiment of the diagnostic method of the invention, the denaturation step of the cycle is performed for 1 minute at 94° C.

The hybridization step of the cycle of the method of in vitro diagnosis of the invention is advantageously carried out by placing the nucleic acid single strands obtained during the denaturation step of the cycle in contact with at least one primer couple of the invention, these primers being selected such that one of the two primers hybridizes with a nucleotide sequence situated on one of the two strands, whereas the other hybridizes with a nucleotide sequence situated on a strand complementary to this latter, the said nucleotide sequences (with which the said primers are capable of hybridizing) being separated by a number of base pairs varying between 50 and 10,000, and preferably between 100 and 2000, when the two complementary strands mentioned above are considered to be incorporated in a double-stranded nucleic acid.

The use of several different primer couples of the invention makes possible the amplification and detection of different nucleotide sequences of the HIV-2 genome.

As examples of preferred primer couples which can be used in the framework of the present invention, mentioned may be made of the primers LTR1 and GAG2. Mentioned may also be made of the couples P1 and P2, P2 and P7, P7 and P8, P8 and LTR2. Advantageously, the primer couples used are selected such that the DNA fragments synthesized cover the regions P1 to P2, LTR1 to Po12, P2 to P7, P7 to P8, P8 to LTR2.

The agent of polymerization used in the elongation step of the cycle is a DNA polymerase, in particular the Taq polymerase or any other polymerase suitable for the implementation of a method of in vitro diagnosis according to the invention following the principle of the "QβReplicase technique" or that described in the International patent application mentioned above.

Generally speaking, the cycle of the method of in vitro diagnosis of the invention is repeated between 10 and 60 times, and preferably 40 times.

Advantageously, the elongation step of the cycle of the above-mentioned method of the invention is carried out for 1 minute at 72° C.

As an example for 1 µg of the retroviral DNA to be detected, 10 pmoles of each primer, 10 nanomoles of each nucleoside triphosphates (dNTP), 1 U of Taq polymerase are used in a final volume of 100 µl of the buffer:

10 mM Tris, pH 8.3 (measured at 23° C.)
20 mM KCl
2 mM MgCl$_2$
0.01% of gelatin and the mixture is subjected 40 times to the following cycle of thermal treatment:

1 mn at 94° C. (denaturation)
1 mn at about 55–60° C. (hybridization)
1 mn at 72° C. (elongation)

In a preferred embodiment of the method of in vitro diagnosis of the present invention, the detection step of the possible presence of the nucleic acid of a virus of the HIV-2 type in the biological sample is carried out with the aid of one (or more) labelled nucleotide probe(s) capable of hybridizing with the amplified nucleic acid sequencers) and in that the possible hybridization complexes then formed between the probe(s) and the amplified nucleotide sequence (s) to be detected, are detected.

The object of the invention is also the primers such as those described above labelled in particular radioactively or enzymatically, as well as their use as nucleotide probes, in particular within the scope of the method of in vitro diagnosis such as that described above.

The primers of the invention can also be used for the implementation of a method of in vitro diagnosis of the infection of monkeys (macaque, mangabey monkey or green monkey) by a virus of the SIV type, this method duplicating the main characteristics of that described above.

The object of the invention is also diagnostic kits for the implementation of the methods of in vitro diagnosis mentioned above. As an example, a diagnostic kit of the present invention contains:

at least one oligonucleotide primer couple according to the invention, each couple comprising one primer which hybridizes with one of the strands of the nucleic acid sequence to be detected, and one primer which hybridizes with the complementary strand of this latter under the conditions defined above, suitable reagents for the implementation of the cycle of amplification operations, in particular the DNA polymerase and the four different nucleoside triphosphates.

one (or several) labelled probe(s) capable of hybridizing with the amplified nucleotide sequencers) to be detected.

The invention also relates to a procedure for the synthesis of the primers described above.

The object of the invention is also a procedure for the production of one (or several) peptide(s) (or polypeptide(s)) comprising:

a step involving the amplification of the nucleotide sequence coding for this peptide (and advantageously containing a promoter for the translation of this sequence) with the aid of a primer couple according to the invention, the introduction of the said nucleotide sequence thus amplified into an appropriate vector, the transformation of suitable host cells with the aid of the above-mentioned vector, the placing in contact of the host cells thus transformed and the recovery of the peptide produced by these latter.

The invention also relates to the polypeptides corresponding, according to the universal enetic code, to the nucleotide sequences (or primers) described above.

The invention also relates to the use of the above-mentioned peptides as immunogenic agents, in particular in association with a pharmaceutically acceptable vehicle in a pharmaceutical composition.

The invention also relates to a procedure for the preparation of the polypeptides mentioned above, in particular those corresponding according to the universal genetic code to the nucleotide sequences (or primers) described above, this procedure being characterized in that, starting preferably from the C-terminal amino acid, successive amino acid residues are condensed one at a time in the required order, or amino acid residues and previously formed fragments already containing several amino acid residues in the correct order are condensed together, or also several fragments prepared in this way beforehand are condensed together, it being understood that care will be taken to protect beforehand all of the reactive functions borne by these amino acid residues or fragments with the exception of the amine function of the one and the carboxyl function of the other which must normally participate in the formation of the peptide bonds, in particular after activation of the carboxyl function according to the methods known in the synthesis of the peptides, and this is continued in a stepwise manner until the N-terminal amino acid is reached.

For example, recourse will be had to the procedure of peptide synthesis in homogeneous solution described by Houbenweyl in "Methode der Organischen Chemie" (Methods in Organic Chemistry), edited by E. Wunsch, vol. 15-I and II, THIEME STUTTGART, 1974, or to that of peptide synthesis on a solid phase described by R. D. Merrified in "Solid Phase Peptide Synthesis" (J. AM. CHEM. SOC., 45, 2149–2154).

The invention also relates to a procedure for the preparation of the nucleotide sequences (or primers) described above, this procedure comprising the following steps:

- incubation of the genomic DNA, isolated from one of the viruses of the HIV or SIV type mentioned above, with DNAase I, then addition of EDTA and purification by extraction with a phenol/chloroform/isoamyl alcohol mixture (25/24/1), then by ether,
- treatment of the DNA thus extracted by means of Eco R1 methylase in the presence of DTT, and purification by extraction as described above,
- incubation of the DNA thus purified with the 4 deoxynucleoside triphosphates dATP, dCTP, dGTP and dTTP in the presence of T4 DNA polymerase and DNA ligase of *E.coli*, then purification according to the method described above,
- the cloning of the nucleic acids thus obtained in a suitable vector and the recovery of the desired nucleic acid with the aid of a suitable probe.

A particularly advantageous procedure for the preparation of the nucleotide sequences of the invention comprises the following steps:

- the synthesis of DNA by using the automated β-cyanoethyl phosphoramidite method described in Bioorganic Chemistry 4, 274–325 (1986),
- the cloning of the nucleic acids thus obtained in a suitable vector and the recovery of the nucleic acid by hybridization with a suitable probe.

Another procedure for the preparation of the nucleotide sequences of the invention comprises the following steps:

- the assembly of chemically synthesized oligonucleotides, provided at their ends with various restriction sites, the sequences of which are compatible with the amino acid sequence of the natural polypeptide according to the principle described in Proc. Natl. Acad. Sci. USA, 80, 7461–7465, (1983),
- the cloning of the nucleic acids thus obtained in a suitable vector and the recovery of the desired nucleic acid by hybridization with a suitable probe.

We claim:

1. An oligonucleotide primer selected from the group consisting of:
nucleotides 40–61 (SEQ ID NO:1);
nucleotides 9537–9558 (SEQ ID NO: 17);
nucleotides 240–259 (SEQ ID NO:18);
nucleotides 546–569 (SEQ ID NO:3);
nucleotides 906–927 (SEQ ID NO:19);
nucleotides 612–633 (SEQ ID NO:5);
nucleotides 1857–1876 (SEQ ID NO:7);
nucleotides 2078–2101 (SEQ ID NO:20);
nucleotides 6275–6299 (SEQ ID NO:9);
nucleotides 6855–6878 (SEQ ID NO:11);
nucleotides 7548–7573 (SEQ ID NO:21);
nucleotides 7782–7805 (SEQ ID NO: 13);
nucleotides 8412–8434 (SEQ ID NO: 14);
nucleotides 61–82 (SEQ ID NO:22); and
nucleotides 9558–9579 (SEQ ID NO:22)
of the genome of HIV-2 ROD virus, and nucleotide sequences complementary thereto.

2. The oligonucleotide primer of claim 1 further comprising at the 5' end a sequence of nucleotides identical to the nucleotides found 5' to a corresponding region of said genome, wherein the number of nucleotides of the primer with the 5' sequence is not greater than 25 nucleotides.

3. An oligonucleotide primer, which hybridizes with the primer of claim 1 under the following hybridization conditions: a solution comprising 10 mM Tris, 20 mM KCl, 2 mM MgCl$_2$ and 0.01 percent of gelatin for one minute at a temperature equal to or higher than 50° C.

4. An oligonucleotide primer selected from the group consisting of:
nucleotides 40–61 (SEQ ID NO:1);
nucleotides 9511–9532 (SEQ ID NO:1);
nucleotides 240–259 (SEQ ID NO:18);
nucleotides 256–275 (SEQ ID NO:18);
nucleotides 551–574 (SEQ ID NO:3);
nucleotides 911–932 (SEQ ID NO:19);
nucleotides 617–638 (SEQ ID NO:5);
nucleotides 1868–1887 (SEQ ID NO:7);
nucleotides 2035–2058 (SEQ ID NO:20);
nucleotides 6227–6251 (SEQ ID NO:23);
nucleotides 7550–7564 (SEQ ID NO:24);
nucleotides 7776–7799 (SEQ ID NO:13);
nucleotides 8406–8428 (SEQ ID NO:25);
nucleotides 61–82 (SEQ ID NO:22); and
nucleotides 9532–9553 (SEQ ID NO:22)
of the genome of SIVmac 142 virus, and nucleotide sequences complementary thereto.

5. The oligonucleotide primer of claim 4 further comprising at the 5' end a sequence of nucleotides identical to the nucleotides found 5' to a corresponding region of said genome, wherein the length of the primer with the 5' sequence is not greater than 25 nucleotides.

6. An oligonucleotide primer, which hybridizes with the primer of claim 4 under the following hybridization conditions: a solution comprising 10 mM Tris, 20 mM KCl, 2 mM MgCl$_2$ and 0.01 percent of gelatin for one minute at a temperature equal to or higher than 50° C.

7. An oligonucleotide primer selected from the group consisting of:

| | | |
|---|---|---|
| GGTTCTCTCCAGCACTAGCAGG | (LTR1), | SEQ ID NO: 1; |
| GGTCCTAACAGACCAGGGTC | (LTR2), | SEQ ID NO: 2; |
| ATGGGCGCGAGAAACTCCGTCTTG | (GAG1), | SEQ ID NO: 3; |
| ATGGTGCTGTTGGTCTACTTGT | (GAG5), | SEQ ID NO: 4; |
| CCCGGCGGAAAGAAAAAGTACA | (GAG2), | SEQ ID NO: 5; |
| TGTACTTTTTCTTTCCGCCGGG | (GAG2B), | SEQ ID NO: 6; |
| TGGGGAAAGAAGCCCCGCAA | (POL1), | SEQ ID NO: 7; |
| CCAAAGAGAATTGAGGTGCAGC | (POL2), | SEQ ID NO: 8; |
| CAGAAATAGGGATACTTGGGGAACC | (P1), | SEQ ID NO: 9; |
| GCCTGAATAATTGGTATCATTACA | (P2), | SEQ ID NO: 10; |
| TGTAATGATACCAATTATTCAGGC | (P2B), | SEQ ID NO: 11; |
| AGTTCTGCCACCTGTGCACTAAAGG | (P4), | SEQ ID NO: 12; |
| GGGATAGTGCAGCAACAGCAACAG | (P6), | SEQ ID NO: 13; |
| CATTTCCTGATCCGCCAGCTGAT | (P7), | SEQ ID NO: 14; |
| ATCAGCTGGCGGATCAGGAAATG | (P7B), | SEQ ID NO: 15; | and

| | | |
|---|---|---|
| GCAGGGAACACCCAGGCTCTAC | (P8), | SEQ ID NO: 16; |

8. The oligonucleotide primer of claim 7, wherein the primer comprises at least one mutation that does not affect the hybridization properties of said primer, wherein the hybridization is detected under the following conditions: a solution comprising 10 mM Tris, 20 mM KCl, 2 mM MgCl$_2$ and 0.01 percent of gelatin for one minute at a temperature equal to or higher than 50° C.

9. A method of in vitro diagnosis of infection of an individual by HIV-2, said method comprising detecting HIV-2 nucleic acid by
a) obtaining a biological sample from said individual wherein said biological sample comprises nucleic acid;
b) extracting HIV-2 nucleic acid from said biological sample and treating said HIV-2 nucleic acid with a reverse transcriptase to produce a double-stranded nucleic acid comprising said HIV-2 nucleic acid and its complementary strand;
c) a cycle comprising the following steps:
denaturing of the double-stranded nucleic acid to be detected, forming single-stranded nucleic acids,
hybridizing of each of said single-stranded nucleic acids with at least one primer according to any one of claims 1–8, by placing said single-stranded nucleic acids in contact with said at least one primer under hybridization conditions,
amplifying said single-stranded nucleic acids by elongation of the primers along the strands to which they are hybridized in the presence of a polymerase, dATP, dGTP, dCTP and dTTP, said cycle being repeated 10 to 60 times; and
d) detecting the presence of amplified nucleic acid of HIV-2.

10. The diagnostic method of claim 9, wherein the hybridization step of the cycle is carried out by placing each of said single-stranded nucleic acids in contact with said primers, wherein said primers hybridize with a nucleotide sequence situated on the first strand of said double-stranded nucleic acid and with a nucleotide sequence situated on the strand complementary to said first strand, said nucleic acid sequences being separated by a region of 50 to 10,000 base pairs when said complementary strands are hybridized to form one double-stranded nucleic acid.

11. The method of claim 10, wherein said region is 100 to 2000 base pairs.

12. The method according to claim 10, wherein said region is selected from the group consisting of LTR1 to Pol2, P1 to P2, P2 to P7, P7 to P8, and P8 to LTR2, of HIV-2.

13. The method according to claim 10, wherein said primers are LTR1 and GAG2; P1 and P2; P2 and P7; P7 and P8; or P8 and LTR2.

14. The method according to claim 9, wherein said detecting step (d) comprises hybridization of at least one detectably labelled nucleotide probe to said amplified nucleotide sequence.

15. A diagnostic kit for the in vitro diagnosis of the infection of an individual by HIV-2 by detecting the presence of HIV-2 nucleic acid or a strand of DNA complementary to said nucleic acid, said kit comprising a) at least a first and a second primer according to any one of claims 1–8, wherein said first primer is complementary to a region of nucleotides of the nucleic acid of HIV-2, and said second primer is complementary to a region of nucleotides of the strand of DNA complementary to said nucleic acid of HIV-2, wherein said regions of nucleotides are separated by 50 to 10,000 base pairs when said complementary strands are incorporated into one double-stranded nucleic acid;

b) reagents for amplifying said nucleic acid; and c) at least one detectably labelled probe, which hybridizes with the amplified nucleotide sequence to be detected.

16. A diagnostic kit for the in vitro detection of nucleic acid of SIV in a biological sample by detecting the presence of SIV nucleic acid or a strand of DNA complementary to said nucleic acid, said kit comprising a) at least a first and a second primer according to any one of claims 1–8, wherein said first primer is complementary to a region of nucleotides of the nucleic acid of SIV, and said second primer is complementary to a region of nucleotides of the strand of DNA complementary to said nucleic acid of SIV, wherein said regions of nucleotides are separated by 50 to 10,000 base pairs when said complementary strands are incorporated into one double-stranded nucleic acid;

b) reagents for amplifying said nucleic acid; and c) at least one detectably labelled probe, which hybridizes with the amplified nucleotide sequence to be detected.

17. A method for the preparation of a polypeptide encoded by a region of the HIV-2 or SIV genome, said method comprising:

a) amplifying of the nucleotide sequence coding for said polypeptide with at least two primers according to any one of claims 1–8, wherein said first primer is complementary to a region of nucleotides of the nucleic acid of said genome, and said second primer is complementary to a region of nucleotides of the strand of DNA complementary to said nucleic acid of said genome, wherein said regions of nucleotides are separated by 50 to 10,000 base pairs when said complementary strands are hybridized to form one double-stranded nucleic acid;

b) introducing the amplified nucleotide sequence into a vector;

c) transforming a host cell with the vector containing the amplified nucleic acid sequence; and d) placing in culture of the transformed host cell and the recovery of said polypeptide.

18. A polypeptide expressed using the method of claim 17.

* * * * *

SEQUENCE LISTING

```
<160> NUMBER OF SEQ ID NOS: 25

<210> SEQ ID NO 1
<211> LENGTH: 22
<212> TYPE: DNA
<213> ORGANISM: Human immunodeficiency virus type 2
<220> FEATURE:

<400> SEQUENCE: 1
ggttctctcc agcactagca gg                                             22

<210> SEQ ID NO 2
<211> LENGTH: 20
<212> TYPE: DNA
<213> ORGANISM: Human immunodeficiency virus type 2
<220> FEATURE:

<400> SEQUENCE: 2
ggtcctaaca gaccagggtc                                                20

<210> SEQ ID NO 3
<211> LENGTH: 24
<212> TYPE: DNA
<213> ORGANISM: Human immunodeficiency virus type 2
<220> FEATURE:

<400> SEQUENCE: 3
atgggcgcga gaaactccgt cttg                                           24

<210> SEQ ID NO 4
<211> LENGTH: 22
<212> TYPE: DNA
<213> ORGANISM: Human immunodeficiency virus type 2
```

-continued

```
<220> FEATURE:

<400> SEQUENCE: 4
atggtgctgt tggtctactt gt                                            22

<210> SEQ ID NO 5
<211> LENGTH: 22
<212> TYPE: DNA
<213> ORGANISM: Human immunodeficiency virus type 2
<220> FEATURE:

<400> SEQUENCE: 5
cccggcggaa agaaaaagta ca                                            22

<210> SEQ ID NO 6
<211> LENGTH: 22
<212> TYPE: DNA
<213> ORGANISM: Human immunodeficiency virus type 2
<220> FEATURE:

<400> SEQUENCE: 6 tgtactttt ctttccgccg gg                                             22

<210> SEQ ID NO 7
<211> LENGTH: 20
<212> TYPE: DNA
<213> ORGANISM: Human immunodeficiency virus type 2
<220> FEATURE:

<400> SEQUENCE: 7
tggggaaaga agccccgcaa                                               20

<210> SEQ ID NO 8
<211> LENGTH: 24
<212> TYPE: DNA
<213> ORGANISM: Human immunodeficiency virus type 2
<220> FEATURE:

<400> SEQUENCE: 8
ccaaagagag aattgaggtg cagc                                          24

<210> SEQ ID NO 9
<211> LENGTH: 25
<212> TYPE: DNA
<213> ORGANISM: Human immunodeficiency virus type 2
<220> FEATURE:

<400> SEQUENCE: 9
cagaaatagg gatacttggg gaacc                                         25

<210> SEQ ID NO 10
<211> LENGTH: 24
<212> TYPE: DNA
<213> ORGANISM: Human immunodeficiency virus type 2
<220> FEATURE:

<400> SEQUENCE: 10
gcctgaataa ttggtatcat taca                                          24

<210> SEQ ID NO 11
<211> LENGTH: 24
<212> TYPE: DNA
<213> ORGANISM: Human immunodeficiency virus type 2
<220> FEATURE:
```

-continued

```
<400> SEQUENCE: 11
tgtaatgata ccaattattc aggc                                    24

<210> SEQ ID NO 12
<211> LENGTH: 25
<212> TYPE: DNA
<213> ORGANISM: Human immunodeficiency virus type 2
<220> FEATURE:

<400> SEQUENCE: 12 agttctgcca

-continued

```
gaccctggtc tgttaggacc                                              20

<210> SEQ ID NO 19
<211> LENGTH: 22
<212> TYPE: DNA
<213> ORGANISM: Human immunodeficiency virus type 2
<220> FEATURE:

<400> SEQUENCE: 19
acaagtagac caacagcacc at                                           22

<210> SEQ ID NO 20
<211> LENGTH: 24
<212> TYPE: DNA
<213> ORGANISM: Human immunodeficiency virus type 2
<220> FEATURE:

<400> SEQUENCE: 20
gctgcacctc aattctctct ttgg                                         24

<210> SEQ ID NO 21
<211> LENGTH: 26
<212> TYPE: DNA
<213> ORGANISM: Human immunodeficiency virus type 2
<220> FEATURE:

<400> SEQUENCE: 21
acctttagtg cagaggtggc agaact                                       26

<210> SEQ ID NO 22
<211> LENGTH: 22
<212> TYPE: DNA
<213> ORGANISM: Human immunodeficiency virus type 2
<220> FEATURE:

<400> SEQUENCE: 22
gtagagcctg ggtgttccct gc                                           22

<210> SEQ ID NO 23
<211> LENGTH: 25
<212> TYPE: DNA
<213> ORGANISM: Simian immunodeficiency virus
<220> FEATURE:

<400> SEQUENCE: 23
caagaatagg gatacttggg gaaca                                        25

<210> SEQ ID NO 24
<211> LENGTH: 15
<212> TYPE: DNA
<213> ORGANISM: Simian immunodeficiency virus
<220> FEATURE:

<400> SEQUENCE: 24
agaggtggca gaact                                                   15

<210> SEQ ID NO 25
<211> LENGTH: 23
<212> TYPE: DNA
<213> ORGANISM: Simian immunodeficiency virus
<220> FEATURE:

<400> SEQUENCE: 25
catttcctga tccgccaact gat                                          23
```